US006265626B1

(12) United States Patent
Carr et al.

(10) Patent No.: US 6,265,626 B1
(45) Date of Patent: *Jul. 24, 2001

(54) SIMULATED COUNTERCURRENT MOVING BED CHROMATOGRAPHIC REACTOR AND METHOD FOR USE THEREOF

(75) Inventors: Robert W. Carr, Minneapolis, MN (US); Anna Lee Y. Tonkovich, Pasco, WA (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/469,801

(22) Filed: Jun. 6, 1995

Related U.S. Application Data (63) Continuation of application No. 08/128,842, filed on Sep. 29, 1993.

(51) Int. Cl.[7] .............................. C07C 27/26; C07C 29/88
(52) U.S. Cl. .................... 568/915; 422/188; 422/189; 585/943
(58) Field of Search .................... 422/187, 188, 422/189, 190, 194; 585/500, 800, 802, 820, 809, 636; 568/915

(56) References Cited

U.S. PATENT DOCUMENTS

| | | | |
|---|---|---|---|
| 3,389,075 | * 6/1968 | Addison | 422/189 |
| 4,001,112 | 1/1977 | Barker et al. | 210/659 |
| 4,104,078 | 8/1978 | Barker et al. | 127/46.1 |
| 4,404,037 | 9/1983 | Broughton | 127/55 |
| 4,491,604 | * 1/1985 | Lesk et al. | 427/8 |
| 4,654,458 | * 3/1987 | Jezc et al. | 585/500 |
| 4,973,453 | * 11/1990 | Agee | 422/190 |
| 5,012,028 | * 4/1991 | Gupta et al. | 585/500 |
| 5,127,957 | 7/1992 | Heikkila et al. | 127/47 |

OTHER PUBLICATIONS

"Ion exchange for esterification" *The Chemical Engineer*, Dec. 10, 1992 pp. 14–15.
"The Simulated Countercurrent Moving Bed Chromatographic Reactor," *Chemical Engineering Science*, Ray, et al. vol. 45, No. 8, pp. 2431–2437, 1990.
"Esterification using solid acid catalysts," Lundquist, et al.
"Methane–C2 Conversion," Joseph Haggin, C&EN, Oct. 11, 1993, pp. 4–5.
"Continuous Chromatographic Processes," *Adsorption: Science and Technology* Barker PE and Ganetsos G, Series E: Applied Sciences—vol. 158.
"Molex: Case History of a Process," D. B. Broughton, *Chemical Engineering Progress*, vol. 64, No. 8, Aug., 1968.
"The Parex Process for Recovering Paraxylene," Broughton, et al. *Chemical Engineering Progress*, vol. 66, No. 9, Sep., 1970.
"Continuous Reaction Chromatography," Robert W. Carr, *Preparation and Production Scale Chromatography*, vol. 61, Mar., 1993, pp. 421–447.
"A New Process Combining Adsorption and Enzyme Reaction for Producing Higher–Fructose Syrup," Hashimoto, *Biotechnology and Bioengineering*, vol. XXV, pp. 2371–2393.

(List continued on next page.)

*Primary Examiner*—Jill Warden
(74) *Attorney, Agent, or Firm*—Schwegman, Lundberg, Woessner & Kluth, P.A.

(57) ABSTRACT

A method and apparatus for continuously reacting a feed gas to form a product and separating the product from unreacted feed gas is provided. The apparatus includes a plurality of compartments and means for connecting the compartments in a series, with the last compartment in the series being connected to the first compartment in the series to provide a closed loop. Each compartment may include an upstream reaction zone and a downstream separation zone.

11 Claims, 7 Drawing Sheets

OTHER PUBLICATIONS

P. E. Barker et al., "A Circular Chromatography Machine for the Preparative Separation of Liquid or Gaseous Mixtures," *Gas Chromatography*, Sep. 20–23, 1996, pp. 135–149.

A.L.Y. Tonkovich, "The Simulated Countercurrent Chromatographic Reactor and Separator," *A Thesis Submitted to the Faculty of the Graduate School of the University of Minnesota*, Jul. 1992, pp. 1–210 (including Table of Contents (i–xii)).

A. K. Ray, "The Simulated Countercurrent Moving Bed Chromatographic Reactor: A Novel Reactor–Separator," *A Thesis Submitted to the Faculty of the Graduate School of the University of Minnesota*, Jun. 1992, Title page and Table Contents (pp. iv–vii).

H.D. Gesser, et al., "The Direct Conversion of Methane to Methanol by Controlled Oxidation", *Chem. Revs.*, 85 , 235 (1985).

N.R. Foster, "Direct Catalytic Oxidation of Methane to Methanol—A Review", *Appl. Catal.*, 19 , 1 (1985).

N.R. Hunter, et al., "The Direct Conversion of Methane to Methanol", *Proc. Vi Int'l. Symp. on Alcohol Fuels Technol.*, vol. II, 2 (1984).

G. Koenig, *Appl. Catal.*, 6 , 263 (1983).

* cited by examiner

SIMULATED COUNTERCURRENT MOVING BED CHROMATOGRAPHIC REACTOR AND METHOD FOR USE THEREOF

This is a continuation of application Ser. No. 08/128,842 filed Sep. 29, 1993.

GOVERNMENT RIGHTS

This invention was made with the support of the U.S. Government under Department of Energy grant no. DE-FG02-84-ER13256. The U.S. Government has certain rights in the invention.

FIELD OF THE INVENTION

The present invention relates to a method and apparatus for continuously reacting a feed gas to form a product and separating the product from unreacted feed gas.

BACKGROUND OF THE INVENTION

When reaction products can be separated from one another or from the reactants, such as by distilling off a volatile product, the chemical equilibrium composition can be continuously shifted to obtain virtually complete conversion in otherwise equilibrium-limited reactions. If a chemical reaction is carried out in a chromatographic column, reaction and separation can occur simultaneously. The separation that occurs when chemical reactions are carried out in chromatographic columns can be exploited to increase reactant conversions beyond the thermodynamic equilibrium limit that exists in well-mixed reactors. The separation permits reaction products of high purity to be obtained, and if the reaction is equilibrium limited, conversions that are significantly greater than the maximum attainable when the reaction is carried out in the absence of separation may be achieved. For example, separation of the products B and C from one another in a reaction of the type $A \rightleftharpoons B+C$ prevents the reverse reaction, so that A may be entirely converted into B and C.

The low throughput that inevitably results from periodic injection of reactants severely limits the use of conventional reaction chromatography for practical chemical processes. Scale-up of these essentially batch processes must be done by increasing the column diameter. Large diameter columns, however, often lead to poor peak resolution due to column packing nonuniformities. Although this problem has been overcome in some instances for use in production scale gas chromatography, the technique is not generally available.

The problem of low throughput has been addressed by the use of a continuous chromatographic reactor, which permits a reaction to be carried out continuously with the separation of individual chemical species. This has been done with systems, such as those having a rotating cylindrical annulus or a countercurrent moving bed, which permit relative motion between the chromatographic bed and the reactant inlet. The simultaneous reaction and separation of reactants and products in such a single reactor-separator on a continuous basis can provide high purity products, and may shift equilibria to increase the yield of products. Recent research on continuous countercurrent moving bed chromatographic reactors (CMCRs) has shown that conditions may be found where product purities in excess of 99%, and nearly unit conversion of equilibrium limited reactions may be achieved (Cho et al., *Proc. R. Soc. Lond.*, A283, 147–189 (1982); Petroulas et al., *Chem. Eng. Sci.*, 40, 2333–2340 (1985)).

These features make CMCRs attractive candidates for chemical processing. Continuous reaction/separation systems may have economic advantages over more conventional methods, not only because conversions may be enhanced, but because the chromatographic separation will do away with, or at least decrease both the capital and energy costs of separating products and reactants. These process aspects are expected to become increasingly important factors in view of increasing emphasis on regulatory compliance and environmental considerations, which create a need for process improvements to enhance competitiveness.

In a CMCR, granular solids flow slowly past a feedport, against a counterpropagating flow of an inert carrier. A number of problems associated with the solids movement may be experienced, however. A solids handling system for recycling solids must be included in a CMCR system. Problems with solids breakdown and attrition, with the resulting requirement for removal of fines, are often observed. The maintenance of a uniform solid flow may also be a significant problem, particularly in large scale operations using large diameter columns.

The process aspects of a countercurrent moving bed can be simulated by successively switching feed and product take-off streams through a series of inlets located at intervals along a fixed bed or series of compartments. The shift of these positions in the direction of the fluid phase flow simulates movement of solids in the opposite direction. In this way the problems associated with solids flow can be avoided. This type of process (Sorbex) has been very successfully developed by Universal Oil Products (Des Plaines, Ill.) for the separation of binary mixtures. A simulated countercurrent moving bed chromatographic system, however, has not been used to carry out combined reaction-separation operations. Further, studies of simulated countercurrent moving bed chromatographic systems have focussed on liquid-solid systems and very little research has been carried out on gas-solid systems.

SUMMARY OF THE INVENTION

The present invention provides a method and apparatus for continuously reacting a feed gas to produce a reaction mixture, which includes a product, and separating the product from the reaction mixture. One embodiment of the apparatus includes a plurality of compartments and means for connecting the compartments in a series. Each compartment includes a reaction zone and a separation zone. The reaction zone includes a reaction zone inlet port, which is connected to a feed gas line and may be connected to a carrier gas line. The separation zone includes at least one separation zone outlet port. The means for connecting the compartments connect each of the separation zone outlet ports to the reaction zone inlet port of the next compartment in the series and the last compartment in the series to the first compartment of the series to provide a closed loop. The means for connecting the compartments also include takeoff means for recovering product exiting the separation zone outlet port. Each of the separation zones may include an upstream section and a downstream section connected by a section connecting means. The section connecting means includes a separation zone recovery port for recovering product passing through the section connecting means.

According to one embodiment of the method of the present invention, pressurized carrier gas and pressurized feed gas are supplied to the inlet port of a first one of the compartments so that the feed gas reacts in the reaction zone to produce a mixture which includes unreacted feed gas and a product and so that the mixture is passed to the separation zone. In the separation zone, the product is separated from the unreacted feed gas. Carrier gas and unreacted feed gas exiting the separation zone outlet port are transferred to the reaction zone inlet port of the next compartment in the series. The product is recovered from the separation zone of the first one of the compartments at a time different than the unreacted feed transfer. Just prior to transferring the carrier gas and the unreacted feed gas to the reaction zone inlet port, the feed gas supply is switched from the first one of the compartments to the reaction zone inlet port of the next compartment in the series. The feed gas and the unreacted feed gas react in the reaction zone of the next compartment to produce a mixture which includes product and unreacted feed gas and this mixture is passed to the separation zone wherein product is separated. After the transfer of the carrier gas and unreacted feed gas to the reaction zone inlet port and the recovery of the product, the first one of the compartments is purged with the pressurized carrier gas. These steps are repeated so that the compartment in which the reaction and separation occurs advances sequentially around the series of compartments in the closed loop.

In another embodiment of the present method, pressurized feed gas is supplied to the reaction zone inlet port of a first one of the compartments in the series and pressurized carrier gas is supplied to the reaction zone inlet port of the preceding compartment in the series. The feed gas reacts in the reaction zone of the first one of the compartments to produce a mixture which includes a product and unreacted feed gas. The mixture is passed to the upstream section of the separation zone of the first one of the compartments, where the product is separated from the unreacted feed gas. Unreacted feed gas and carrier gas exiting the separation zone outlet port are transferred to the reaction zone inlet port of the next compartment in the series. The product is recovered from the separation zone recovery port of the first one of the compartments at a time after the transfer of the unreacted feed transfer. After the recovery of the product, the first one of the compartments is purged with carrier gas. Just prior to the transfer of the unreacted feed, the feed gas supply is switched from the reaction zone inlet port of the first one of the compartments to the reaction zone inlet port of the next compartment in the series and the carrier gas supply is switched from the reaction zone inlet port of the preceding compartment in the series to the reaction zone inlet port of the first compartment in the series. The feed gas and unreacted feed gas react in the reaction zone of the next compartment to produce the mixture which includes the product and unreacted feed gas. The mixture is passed to the upstream section of the separation zone of the next compartment in the series. The product is separated from the unreacted feed gas and the unreacted feed gas exits the separation zone outlet port. These steps are repeated so that the compartment in which the reaction and separation occurs advances sequentially around the series of compartments in the closed loop.

In yet another embodiment of the present method, a plurality of compartments and means for connecting the compartments in a series are provided. Each compartment includes an inlet port and an outlet port defining a flowpath therebetween and a catalyst/adsorbent mixture interposed in the flowpath. The means for connecting the compartments connect each of the outlet ports to the inlet port of the next compartment in the series and the last compartment in the series to the first compartment of the series to provide a closed loop.

Pressurized feed gas is supplied to the inlet port of a first one of the compartments so that the feed gas reacts to produce a reaction mixture which includes a product and unreacted feed gas, and so that the product is separated from the unreacted feed gas. The unreacted feed gas exits the outlet port of the first compartment in the series and is transferred to the inlet port of the next compartment in the series. After the transfer of the unreacted feed, the product is recovered from the first one of the compartments. Just prior to the transfer of unreacted feed, the feed gas supply is switched from the inlet port of the first one of the compartments to the inlet port of the next compartment in the series. The feed gas and the unreacted feed gas react in the next compartment to produce the mixture which includes the product and unreacted feed gas. The product is separated from the unreacted feed gas and the unreacted feed gas exits the outlet port. These steps are repeated so that the compartment in which the reaction and separation occurs advances sequentially around the series of compartments in the closed loop.

Thus, the present invention provides a method and apparatus which permit the simultaneous reaction of a feed gas to form a product and the separation of the product from unreacted feed gas. Because the present invention allows the reaction and separation to be carried out in a continuous manner, reactions which normally proceed to only very low conversions in conventional systems may be carried out much more efficiently. When viewed simply in terms reactants introduced and products extracted, the conversions which may be obtained using the method and apparatus of the present invention may greatly exceed those realized using conventional systems. In addition, the present invention avoids the problems of solids handling, nonuniform solids flow and solids breakdown which are associated with continuous countercurrent moving bed chromatographic reactors.

DETAILED DESCRIPTION OF THE INVENTION

General Description of the Method

Figure 1:
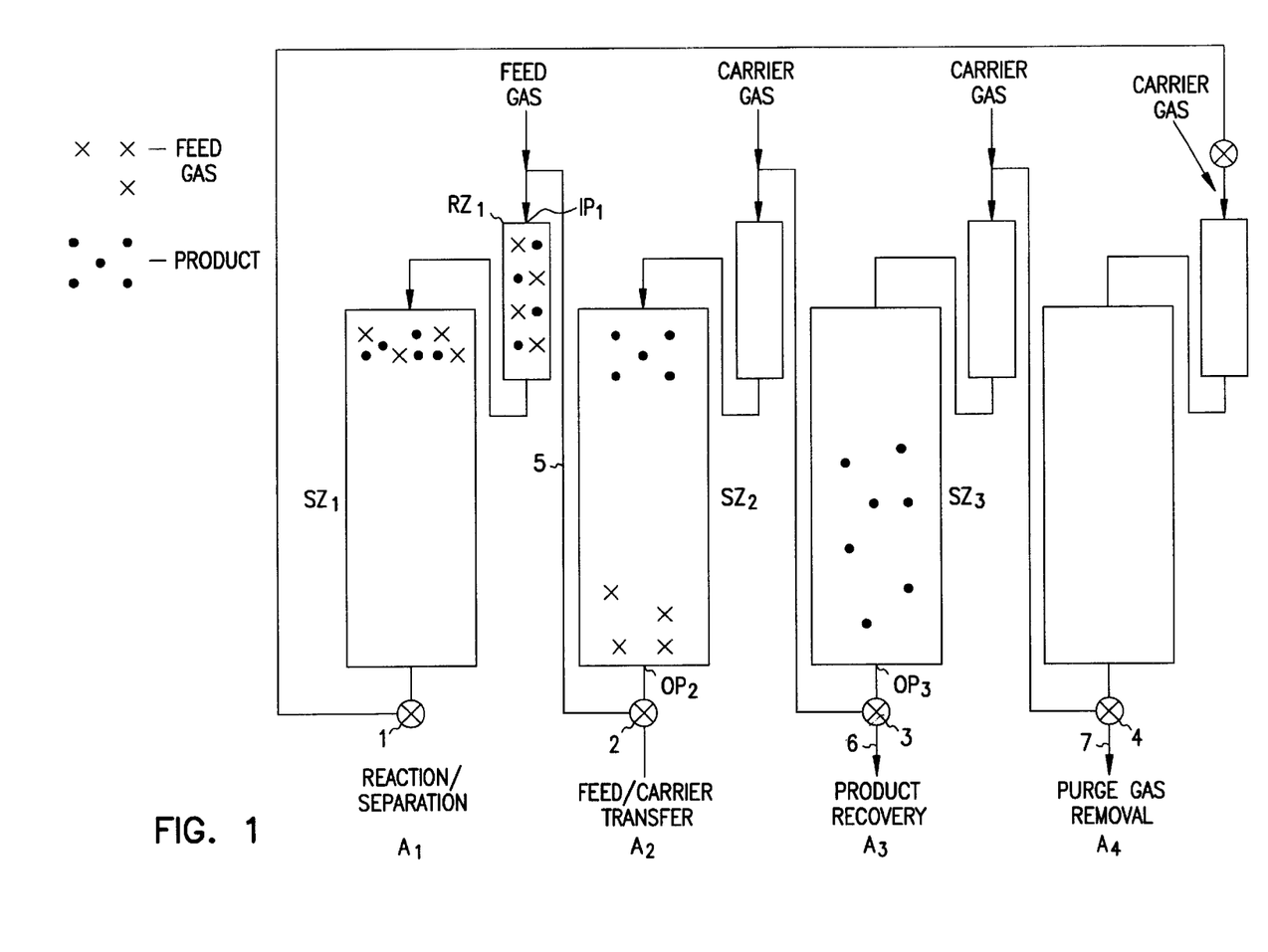
FIG. 1 schematically depicts the present method for reacting a feed to produce a product and for separating the product from unreacted feed.

FIG. 1 shows a general representation of the present method for reacting a feed gas to produce a product and for separating the product from unreacted feed gas. The apparatus shown contains four compartments, designated $A_{1-A4}$, each of which includes a reaction zone and a separation zone. The reaction zone includes a reaction zone inlet port which is connected to a feed gas line, a carrier gas line and a transfer line. The separation zone includes at least one separation zone outlet port. The method and apparatus permit the simultaneous reaction of a feed gas to form a product and separation of the product from unreacted feed gas to be carried out on a continuous basis.

The reaction zone typically includes a catalyst, such as a metal, metal oxide or doped metal oxide. In other instances, the reaction to be carried out may not require a catalyst, e.g., reactions which occur at elevated temperatures. The separation zone includes a means for separating product from unreacted feed gas. Typically, the means for separating product from unreacted feed gas includes an adsorbent, such as activated charcoal or alumina.

In FIG. 1, the status of the compartments is shown just after the supply of feed gas has been switched from compartment $A_2$ to compartment $A_1$. In compartment $A_{21}$ unreacted feed gas in the lower portion of separation zone $SZ_2$ is swept out of the separation zone by the flow of carrier gas through separation zone outlet port $OP_2$. The carrier gas may include any gas which is chemically inert under the conditions found in the system and which is not strongly adsorbed by adsorbents present in the separation zone. Nitrogen, helium and argon are examples of suitable carrier gases. The unreacted feed gas and carrier gas are directed by valve 2 through transfer line 5 to the reaction zone inlet port $IP_1$ of the next compartment in the series, $A_1$. At the same time, makeup feed gas is added to the reaction zone inlet port $IP_1$ to replace any feed gas which was consumed by the reaction in the preceding compartment in the series, $A_2$. The unreacted feed gas from compartment $A_2$ and the makeup feed gas pass through reaction zone inlet port $IP_1$ into reaction zone $RZ_1$ where reaction occurs and the feed gas is partially converted into product. The flow of carrier gas sweeps the mixture of unreacted feed gas and product into separation zone $SZ_1$, where the product and unreacted feed are separated. In the embodiment shown, unreacted feed moves more quickly through the separation zone, producing a distribution of product and unreacted feed such as that seen in compartment $A_2$. Compartment $A_3$ no longer contains any unreacted feed, which has already been swept into the next compartment in the series $A_2$. Valve 3, which has been switched to direct the flow of carrier gas into line 6, permits product to be swept out of separation zone $SZ_3$ through outlet port $OP_3$ into product recovery line 6. Compartment $A_4$, which does not contain any product or unreacted feed gas, is shown being swept with carrier gas to purge any material remaining from the adsorbent in separation zone $SZ_4$. The carrier gas and purged materials are directed by valve 4 into purge gas removal line 7. In an alternate embodiment the product recovery and purge operations may be conducted on a single column by the use of appropriate valving to direct the product recovery and purge gas streams exiting the outlet port into different lines (See descriptions of FIGS. 2 and 7 below).

Description of the Apparatus

Figure 2:
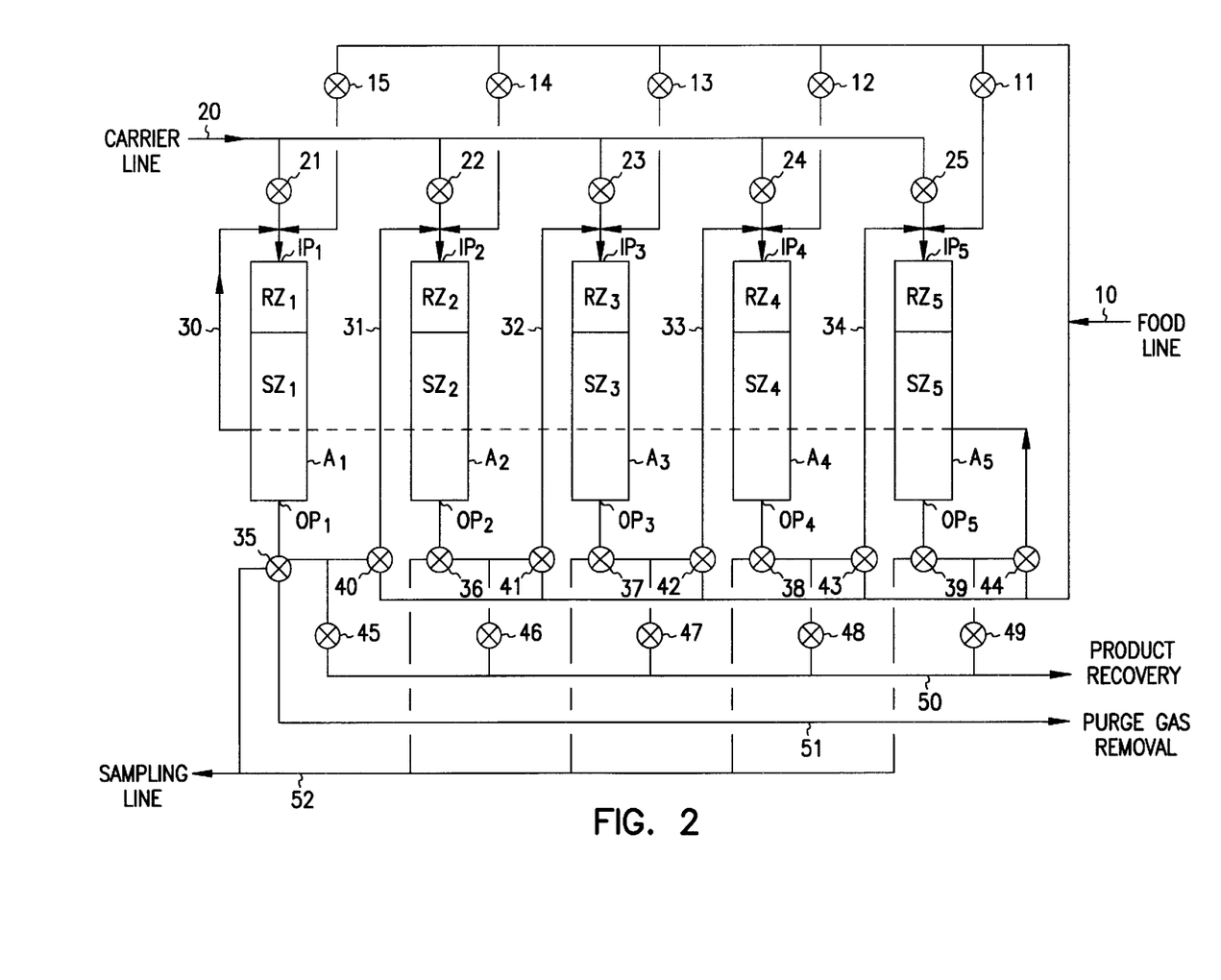
FIG. 2 is a schematic depiction of one embodiment of the simulated countercurrent moving bed chromatographic reactor (SCMCR) apparatus of the present invention.

FIG. 2 is schematic depiction of one embodiment of the simulated counter current moving bed chromatographic reactor apparatus of the present invention. The apparatus shown contains five compartments $A_n$, each of which includes a reaction zone $R_n$ and a separation zone $S_n$. Each reaction zone $RZ_n$ includes a reaction zone inlet port $IP_n$ which is connected to carrier gas line 20 and feed gas line 10. The flow of carrier gas to the inlet ports $IP_n$ is controlled by valves 21–25. The flow of feed gas to the inlet ports $IP_n$ is controlled by valves 11–15. The reaction zone $RZ_n$ may also include a first means for regulating temperature, such as a tube furnace. Each of the separation zones $SZ_n$ includes a separation zone outlet port $OP_n$. The separation zone $SZ_n$ may also include a second means for regulating temperature, such as a gas chromatographic oven. Materials being swept out of the separation zone by the flow of carrier gas exit the compartment $A_n$ through the outlet port $OP_n$. Valves 35–39, which are connected directly to the outlet ports $OP_n$, permit the gas stream exiting the separation zone outlet port $OP_n$ to be directed to the purged gas removal manifold 51 or to the other manifolds shown. A mixture of product and carrier gas exiting an outlet port $OP_n$ may be directed into the product recovery manifold 50 by way of one of a pair of valves 35–39 and 45–49. Valves 35–39 also permit the gas stream exiting an outlet port $OP_n$ to be monitored by periodically directing a small portion of the stream to a detector via sampling line 52. When the gas mixture exiting the outlet port $OP_n$ contains unreacted feed gas mixed with carrier gas, the mixture may be directed to transfer lines 30–34 by way of one of a pair of valves 35–39 and 40–44. Using compartment $A_1$ as an example, this would permit unreacted feed gas and carrier gas to be transferred from outlet port $OP_1$ via valves 35 and 40 and transfer line 31 to the reaction zone inlet port $IP_2$ of compartment $A_2$. The outlet port $OP_n$ of each compartment $A_n$ is connected via the valves and transfer lines to the reaction zone inlet port $IP_{n+1}$ of the next compartment in the series $A_{n+1}$. The outlet port $OP_5$ of the last compartment in the series $A_5$ is connected to the reaction zone inlet port $IP_1$ of the first compartment in the series $A_n$ to form a closed loop.

Figure 3:
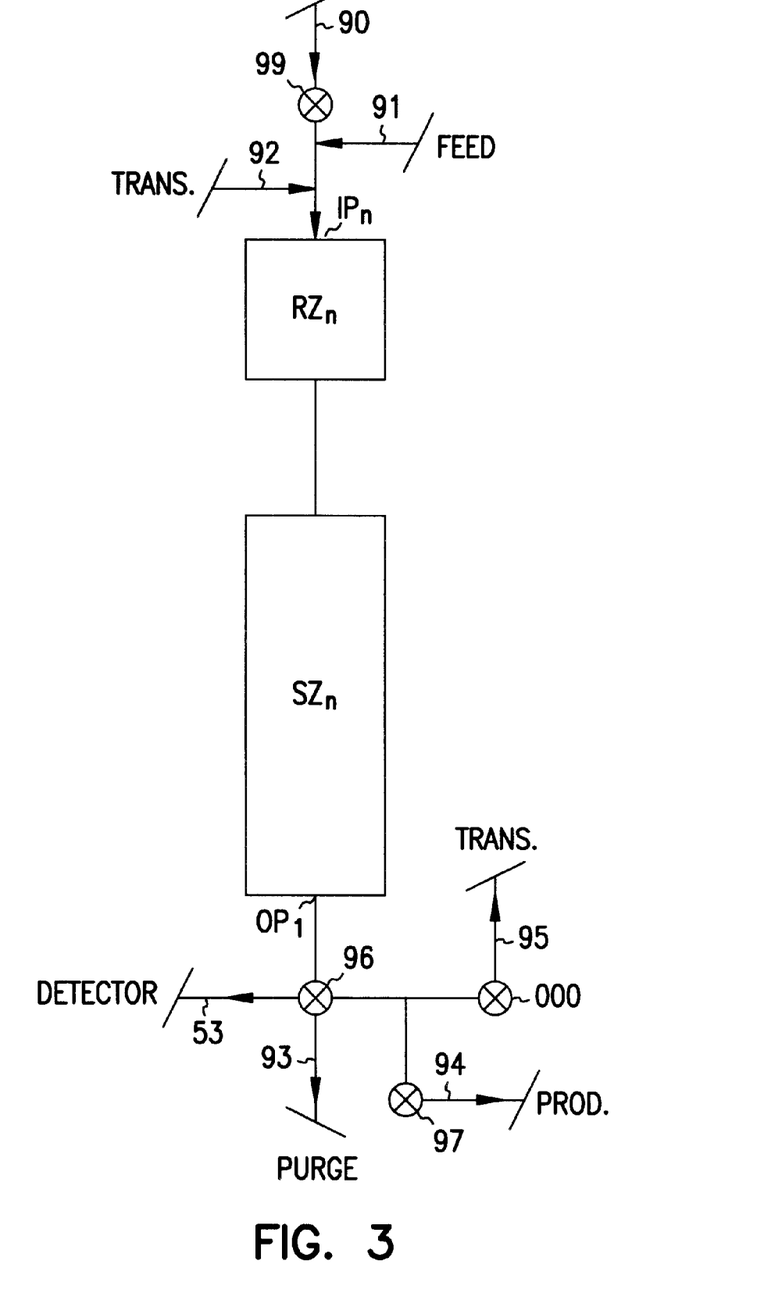
FIG. 3 is a schematic depiction of a single compartment of the apparatus of FIG. 1.

FIG. 3 is a schematic depiction of a single compartment of the apparatus shown in FIG. 2. The compartment includes a reaction zone $RZ_n$ and a separation zone $SZ_n$. The reaction zone $RZ_n$ includes a reaction zone inlet port $IP_n$ which is connected to transfer line 92, feed gas line 91 and carrier gas line 90. Valve 99 permits the inlet port to be isolated from the carrier gas line 90. The separation zone $SZ_n$ includes a separation zone outlet port $OP_n$ which is connected to a valve 96. Valve 96 permits the gas stream exiting the outlet port $OP_n$ to be directed either to product recovery line 94 by way of valve 97, to transfer line 95 by way of valve 98, to sampling line 53 or to purge gas removal line 93.

Figure 4:
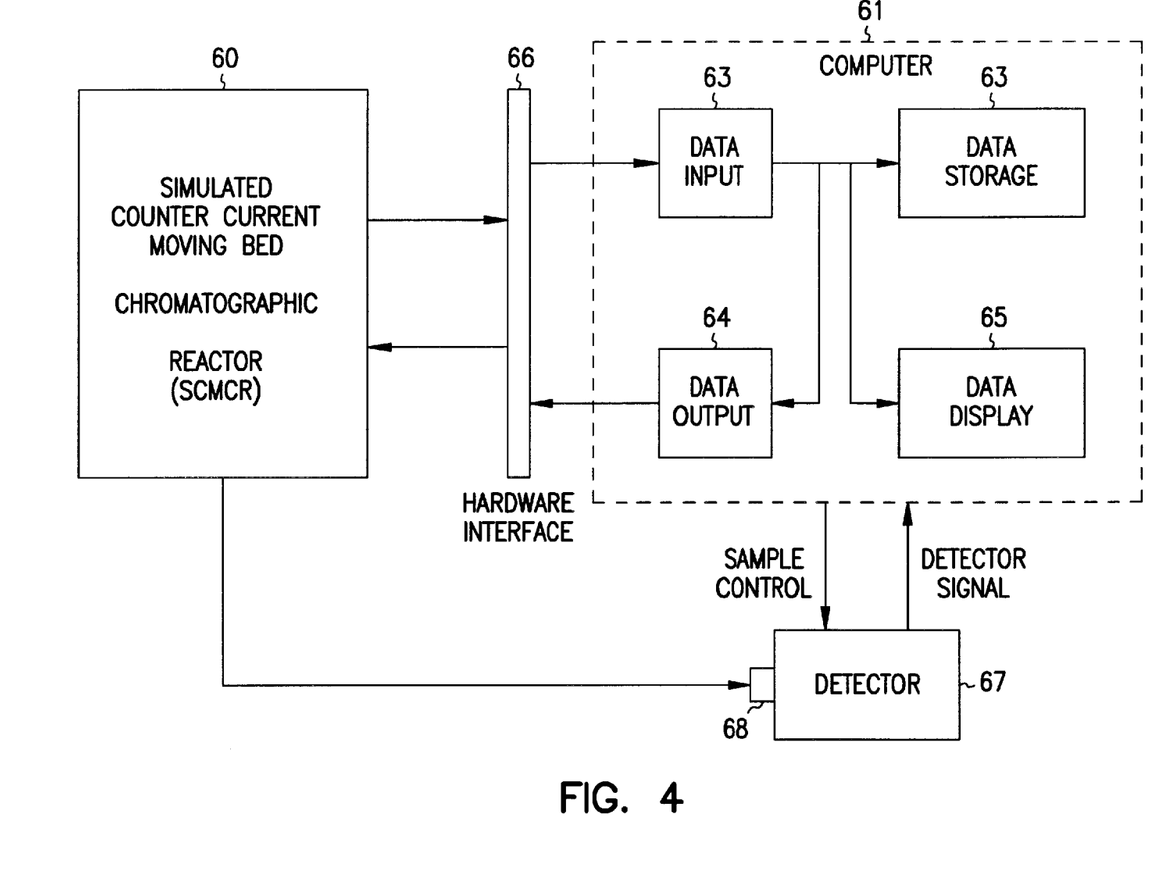
FIG. 4 is a schematic depiction of the controller which is used to control and coordinate the flow of feed gas, carrier gas and product gas in the SCMCR apparatus of the present invention.

FIG. 4 shows a schematic representation of the controller which is used to control and coordinate the flow of feed gas, carrier gas, and product gas in the SCMCR apparatus of the present invention. Gas streams exiting the separating zone outlet ports of the compartments of the SCMCR 60 may be sampled by directing a portion of a given stream to the sampling port 68 of detector 67. For instance, the detector may be a gas chromatograph and the sampling port the injector of the gas chromatograph, Both the SCMCR 60 and the detector 67 are coupled to a computer 61. Data input and output between the SCMCR 60 and the computer 61 passes through a hardware interface 66. The computer 61 includes software/hardware modules to perform data input 62, data storage 63, data output 64, and data display 65. Computer 61 also is coupled to detector 67 to control the sampling of the detector and to receive signals from the detector. The computer 61 monitors the gas streams exiting the separation zone outlet ports of the SCMCR 60 and controls the valves of the SCMCR to coordinate the flow of feed gas, carrier gas, and product and the removal of purged materials in the SCMCR compartments.

Figure 5:
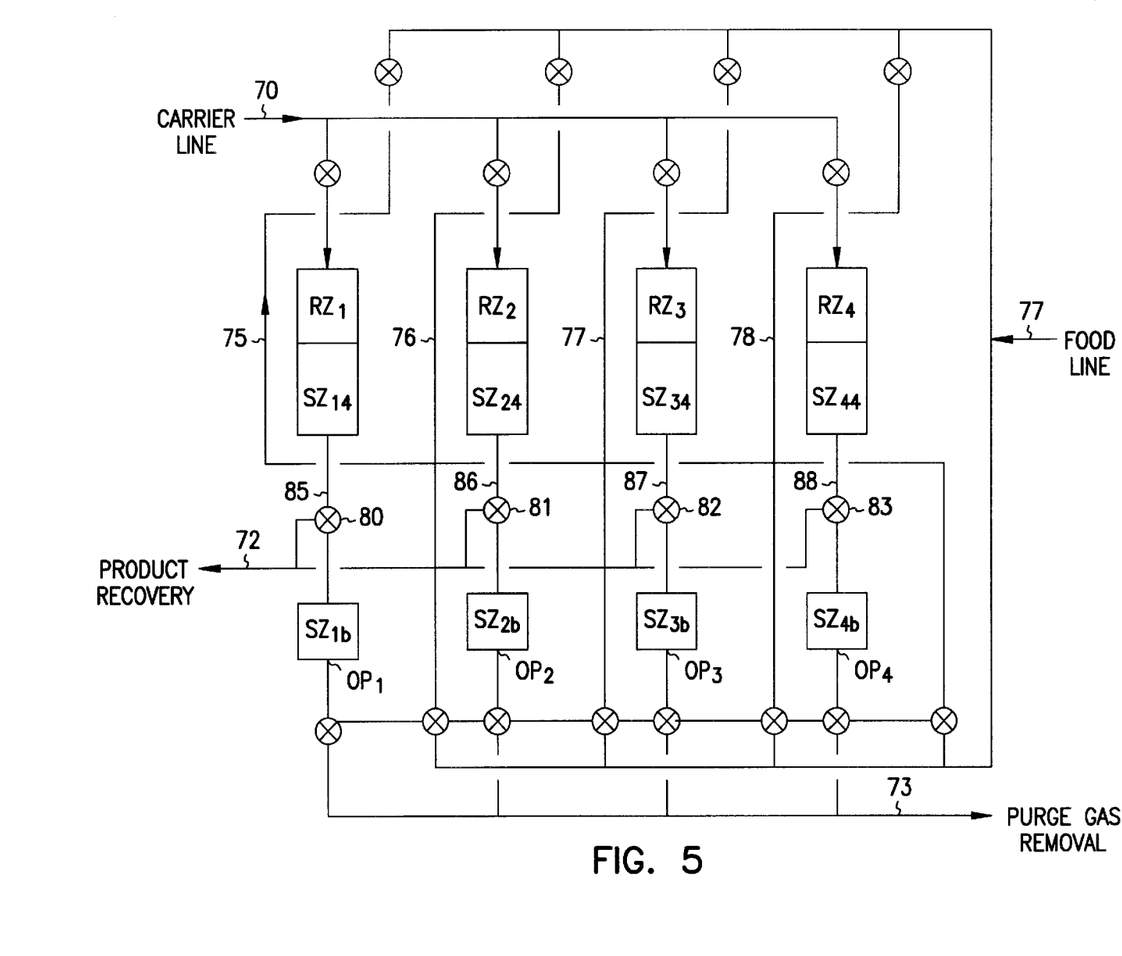
FIG. 5 is a schematic depiction of another embodiment of the simulated countercurrent moving bed chromatographic reactor apparatus of the present invention.

An alternate embodiment of the present invention is shown in FIG. 5 which is a schematic representation of a four-compartment SCMCR apparatus. As with the embodiment shown in FIG. 2, carrier gas line 70 and feed gas line 71 are connected to the reaction zone inlet ports $IP_n$ through sets of valves. In the embodiment shown in FIG. 5, each separation zone includes an upstream section $SZ_{na}$ and a downstream section $SZ_{nb}$. The upstream and downstream sections of each separation zone are connected by section connecting lines 85–88. Each section connecting line is connected to product recovery manifold 72 through one of valves 80–83. This permits a gas stream exiting one of the upstream separation zone sections $SZ_{na}$ to be directed either to the product recovery manifold 72 or to the corresponding downstream separation zone section $SZ_{na}$. As with the embodiment shown in FIG. 2, a gas stream exiting the separation zone outlet port $OP_n$ may be directed either to the purge gas removal manifold 73 or to the next compartment in the series $A_{n+1}$ via one of transfer lines 75–78 by means of the valves shown.

Figure 6:
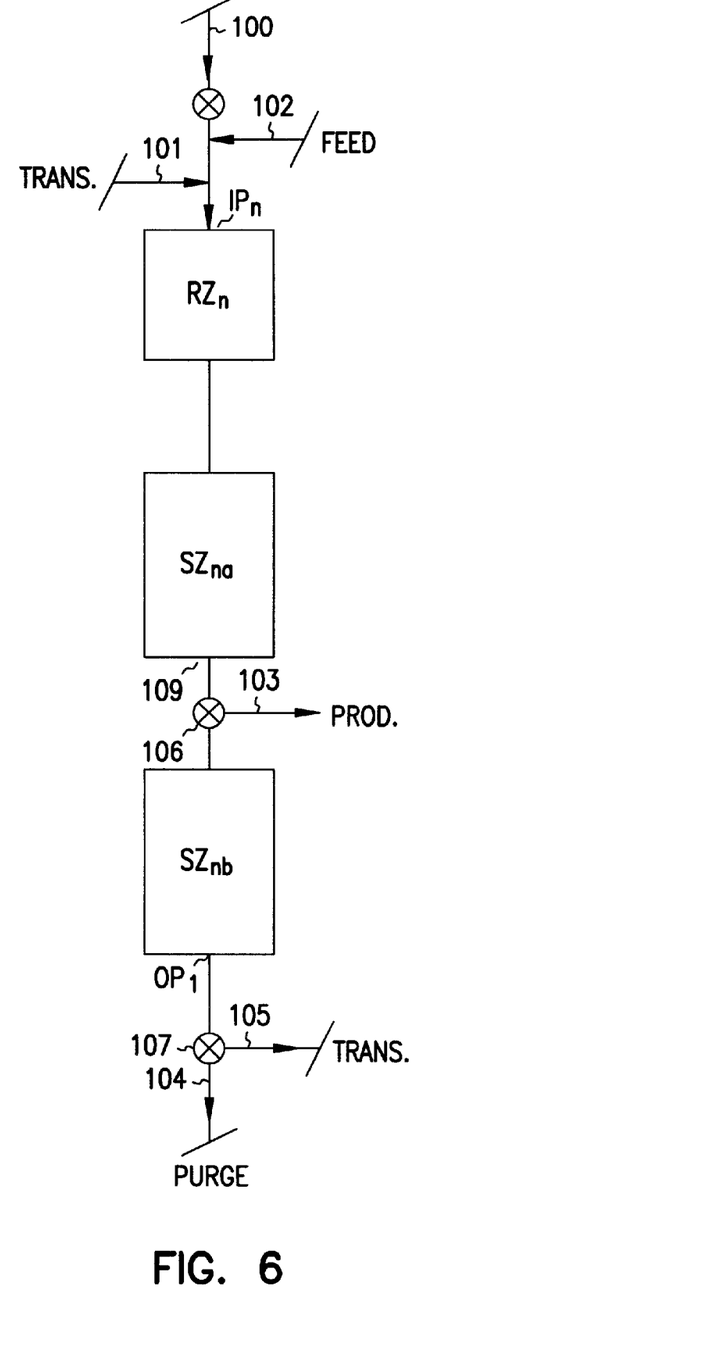
FIG. 6 is a schematic depiction of a single compartment of the apparatus of FIG. 5.

FIG. 6 is a schematic depiction of a single compartment of the SCMCR apparatus shown in FIG. 5. As with the embodiment shown in FIG. 3, the compartment includes a reaction zone and a separation zone. The separation zone includes an upstream separation zone section $SZ_{na}$ and a downstream separation zone section $SZ_{nb}$. The two sections $SZ_{na}$, $SZ_{nb}$ are connected by a section connecting line 109, which includes a valve 106. Valve 106, which acts as a separation zone recovery port, permits a gas stream exiting separation zone section $SZ_{1a}$ to be directed either to the downstream separation zone section $SZ_{1b}$ or to the product recovery line 103. The separation zone outlet port $OP_n$ is connected to purge gas removal line 104 and transfer line 105 through valve 107. As with the embodiment shown in FIG. 5, the reaction zone $RZ_n$ includes a reaction zone inlet port $IP_n$ which is connected to transfer line 101, feed gas line 102 and carrier gas line 100.

Figure 7:
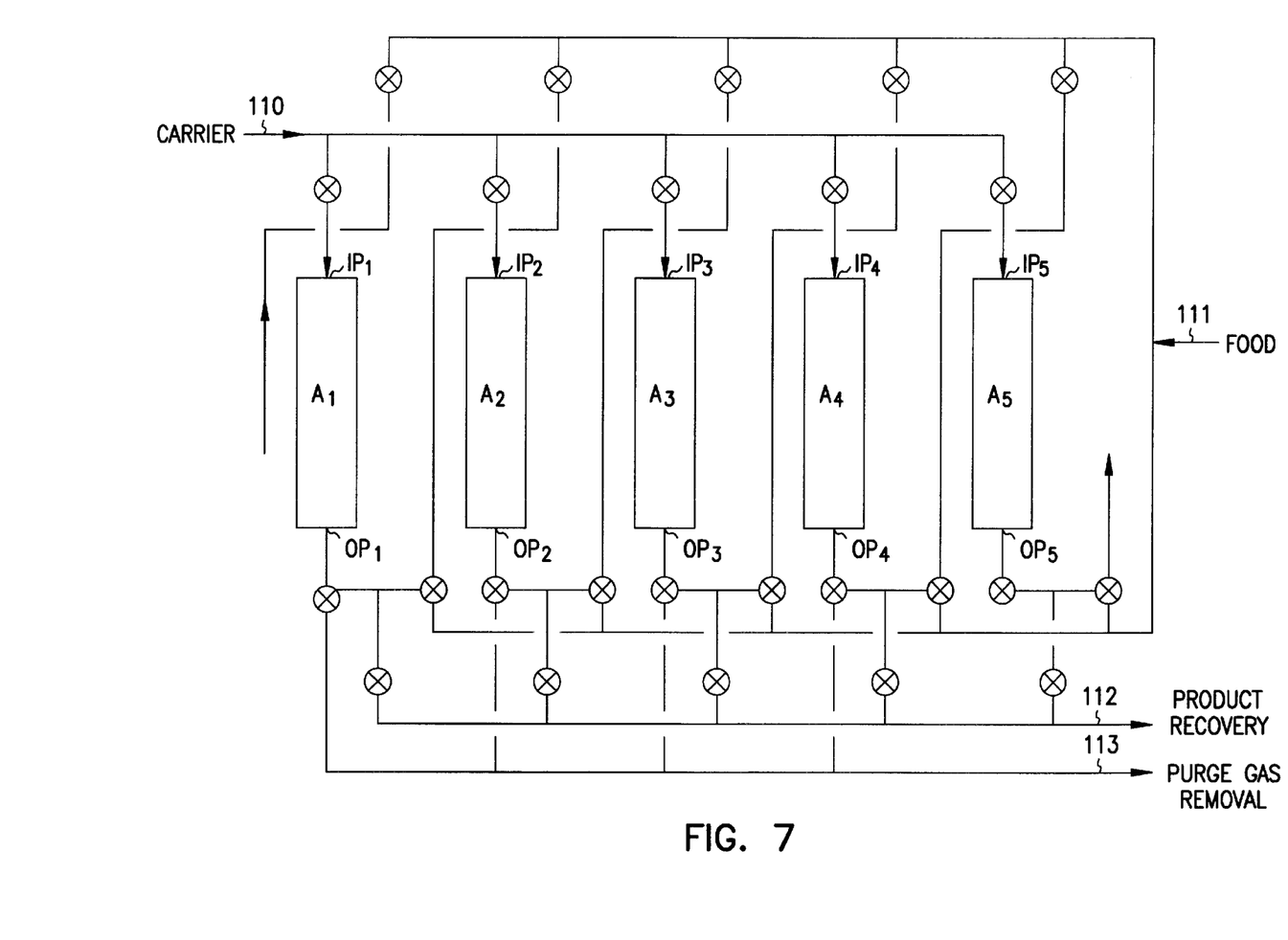
FIG. 7 is a schematic depiction of an alternate embodiment of the simulated countercurrent moving bed chromatographic reactor apparatus of the present invention.

FIG. 7 shows a schematic depiction of another embodiment of the SCMCR apparatus of the present invention. This embodiment includes five compartments $A_1$–$A_5$. As with the other embodiments of the present invention, the inlet port of each of the individual compartments $A_n$ is connected to carrier gas line 110 and feed gas line 111 and each of the outlet ports $OP_n$ is connected to the product recovery manifold 112 and the purge gas removal manifold 113 through the series of valves and transfer lines shown. The compartments $A_n$ shown in FIG. 7 are not divided into distinct reaction and separation zones and permit both reaction and separation to be carried out throughout each compartment. Each compartment typically includes a catalyst/adsorbent mixture which is disposed in the flowpath defined by the inlet and outlet ports of the compartment. For example, if the apparatus is used to carry out the reaction of methane in the presence of oxygen to form methanol, the catalyst/adsorbent mixture may include a copper or cupric oxide catalyst and an alumina adsorbent. In other instances, where the reaction to be carried out may not require a catalyst, e.g., reactions which occur at elevated temperatures, the compartments may include an adsorbent disposed in the flowpath.

In the embodiments of the present invention depicted in FIGS. 1–7, the product is typically recovered by sweeping the compartment with a carrier gas and directing the mixture of product and carrier gas exiting the compartment to a product recovery manifold. In some instances, such as where the product is less strongly adsorbed than the feed gas, the product may be recovered without the aid of a carrier gas. Since the less strongly adsorbed component, the product, will move more rapidly though the compartment, the product may be recovered by initially directing the effluent from the compartment to the product recovery manifold and subsequently switching the effluent to a transfer line once the effluent includes unreacted feed gas. The product may also be recovered from a compartment by other methods. For example, where a compartment no longer contains any unreacted feed gas but still includes product, the compartment may be isolated and the product recovered by passing a desorbent through the compartment or by applying a vacuum to the compartment.

Exemplary Reactions Carried Out in an SCMCR

The metal oxide catalyzed reaction of methane ($CH_4$) in the presence of oxygen ($O_2$) to form ethane ($C_2H_6$) and ethylene ($C_2H_4$) has received much attention, primarily because of interest in converting abundant natural gas reserves to more useful feedstocks. The metal oxide catalyst typically includes $Sm_2O_3$, CaO, BaO, MnO, MgO or SrO, and preferably includes $Sm_2O_3$, MgO or SrO. The metal oxide may be doped with a metal, a metal salt (e.g., alkali metal salt). Although many catalysts exhibit selectivity for the $C_2$ hydrocarbons, the less than stoichiometric $O_2/CH_4$ ratios necessary to minimize complete oxidation result in low $CH_4$ conversions and modest $C_2$ yields. Since the $C_2$ yields are typically no more than about 20% even with the most active and selective catalysts, the commercial feasibility of the process is marginal. By running the process in the SCMCR apparatus of the present invention, the conversion of $CH_4$ and the yield of $C_2$ products may be significantly increased in comparison with the performance attainable in conventional fixed bed or fluidized bed reactors. When the reaction of methane and oxygen to yield ethane and ethylene is run in an SCMCR which includes an $Sm_2O_3$ catalyst in the reaction zone, reaction zone temperatures of about 550° C. to about 1100° C., and preferably about 700° C. to about 900° C., are typically used. Under these reaction conditions, the methane/oxygen ratio in the gas stream initially introduced to the first reaction zone is typically within the range of about 10:1 to about 100:1 and preferably within the range of about 20:1 to about 60:1. Once the feed gas supply is switched and cycled through the series of compartments, the methane/oxygen ratio in the makeup feed gas added to each reaction zone inlet port is controlled such that any feed gas which was consumed by the reaction in the preceding compartment in the series is replaced. In other words, the methane/oxygen ratio in the makeup feed gas is sufficient to maintain the methane/oxygen ratio entering the reaction zone at the desired value. With the $Sm_2O_3$ catalyst, a methane/oxygen ratio of 50:1 and reaction zone temperatures of about 700° C. to about 800° C., methane conversions exceeding 60% and a $C_2$ selectivity of 80 to 90% may be achieved. This corresponds to $C_2$ yields of >50% based on methane feed.

The rapid separation of $O_2$, $CH_4$, and $C_2$ products that occurs in the SCMCR is the key to this process. The oxidative coupling reaction is not equilibrium limited, but is a low-conversion process if further oxidation of the desired products, $C_2H_4$ and $C_2H_6$, as well as complete oxidation of $CH_4$, is to be minimized. Reaction chromatography in the SCMCR permits the separation of $O_2$ and $CH_4$ from the $C_2$ products, thereby suppressing the oxidation of the products. It also permits more extensive $CH_4$ contact with the catalyst and increases the conversion. Finally, the use of SCMCR produces a $C_2$ product stream free not only of $O_2$ but of $CH_4$. The separation of the unreacted methane from the $C_2$ products (ethane and ethylene) may be carried out by passing the mixture of methane and $C_2$ products through a separation zone which includes an activated charcoal adsorbent. During this separation, the separation zone is typically maintained at a temperature of about 0° C. to about 200° C., preferably at about 50° C. to about 150° C. and more preferably at about 100° C.

The direct partial oxidation of methane to methanol in the presence of oxygen is another example of a reaction which would be of commercial interest if better conversions could be achieved. The reaction is typically run in the presence of metal or metal oxide catalysts, such as copper or cupric oxide. The oxidation reaction must be run at low oxygen concentrations to avoid overoxidation of the product. Because of this, yields of only a few percent are typically achieved using conventional reactors.

The conversion and selectivity of the oxidation of methane to methanol in the presence oxygen can be greatly enhanced by running the reaction in an SCMCR. The reaction may be run in either the apparatus shown in FIG. 2 (which has distinct reaction and separation zones) or in the apparatus shown in FIG. 7 (where each compartment includes a catalyst/adsorbent mixture disposed in the flowpath). For example, the direct partial oxidation of methane to methanol in the presence of oxygen may be carried out using the system of FIG. 7, in which the catalyst/adsorbent mixture in each compartment includes alumina and at least one of copper and cupric oxide. The feed gas is typically supplied to the inlet ports such that the methane/oxygen ratio entering the compartments is maintained within the range of about 15:1 to about 100:1. The compartments are maintained at a temperature of about 350° C. to about 500° C. and the total feed gas pressure is maintained at about 30 to about 200 atmospheres. When the oxidation of methane to methanol is carried out under these reaction conditions, the selectivity for methanol may be in the range of 70–90% and methanol yields substantially higher than those obtained in conventional reactors may be realized.

The present invention may be further described by reference to the following example.

EXAMPLE 1

Formation of $C_2$ Hydrocarbons via Oxidative Coupling of Methane

The $Sm_2O_3$ catalyzed reaction of methane in the presence of oxygen to form ethane and ethylene was run using a four-section SCMCR having the configuration shown in FIG. 4. Each reactor zone consisted of a 0.64 outside diameter (OD) quartz tube, which was packed with 70 mg of unpromoted $Sm_2O_3$ powder (Aldrich Chemical) and heated in a tube furnace. The tube furnace was maintained at a constant temperature during any single run. Runs were conducted with tube furnace temperatures ranging from 550° C. to 780° C. Each separation zone consisted of a 19 cm long by 0.64 cm OD aluminum separation column packed with activated charcoal (All-tech) which was contained in a 100° C. gas chromatograph (GC) oven. The separation column was divided into two parts, an 7.6 cm long upstream section ($SZ_{1a}$–$SZ_{4a}$) and a 11.4 cm long downstream section ($SZ_{1b}$–$SZ_{4b}$). The two separation zone sections were connected by a short 0.32 OD section connecting line having a three-way computer-operated solenoid valve which permitted ethane and ethylene passing through the section connecting line to be recovered (See FIG. 6).

The apparatus was fed initially with 18 ml/min of a 50:1 $CH_4$-air mixture and 100 ml/min of $N_2$ carrier gas (measured at ambient temperature). The $CH_4$ and $O_2$ that react were replaced at every feed position advancement thereafter by 1.4 to 1.7 ml/min of a 3:2 $CH_4/O_2$ make-up mixture. This was the value calculated to maintain the $CH_4/O_2$ entering the reaction zones at 50:1. The 100-ml/min carrier was supplied to the compartment behind feed compartment, and $C_2H_6$ and $C_2H_4$ are removed from the separation zone that was two compartments behind the feed compartment after traveling only through the 7.6 cm upstream separation zone section. Because the breakthrough time for the products to pass through the full length of the separation zone was about 4 min, if the products were not removed after passing through the upstream section, the reactant (methane) would overtake it on the next cycle. Nitrogen and oxygen were not separated and filled the entire reactor more or less uniformly. The $C_2$ concentration in the carrier gas at the product take-off was about 1%. Unreacted methane was routed to the next compartment in the series upon breaking through the full length of a separation zone. Just before breakthrough of unreacted methane, the feed position was advanced to the reaction zone of the next compartment in the series by switching the position of the make-up feed ahead to the next compartment. The makeup feed stream was advanced from compartment to compartment at 28 second intervals. The compartment ahead of the feed compartment was purged with $N_2$ at an elevated flow rate. This substantially removed any species that might have remained and prepared the compartment for becoming the feed compartment. All compartment inlet and effluent flows were directed through 0.32-cm OD lines by computer-operated solenoid valves. Reaction product analyses were obtained by automatic sampling analytical gas chromatography.

TABLE I

| Temperature | Conversion | Selectivity |
|---|---|---|
| 550° C. | 46% | 10% |
| 600° C. | 43% | 22% |
| 650° C. | 47% | 55% |
| 700° C. | 65% | 50% |
| 725° C. | 64% | 80% |
| 775° C. | 65% | 78% |

The selectivity and conversion obtained over a temperature range from 550° C. to 775° C. are shown in Table I above. The selectivity and conversion both increased with increasing temperature. The $C_2$ yield, calculated as the product of conversion and selectivity, increased from about 5% between 550 to 600° C. to >50% as the temperature approached 800° C., where the $C_2H_4$ to $C_2H_6$ ratio is about 0.33. This performance can be compared with the reaction of methane and oxygen in a single 725° C. microreactor where the selectivity may exceeds 90%, but the low conversion gives small $C_2$ yields. At the 50:1 methane/oxygen ratio used in the SCMCR experiments, the $C_2$ yield from the microreactor is <3%. This performance is similar to other previously reported for microreactor studies with $Sm_2O_3$ catalyst. Accordingly, the SCMCR provides to an improvement in $C_2$ yield of a factor of >12. The SCMCR performance depended upon the interval between successive switches of feed and on the $CH_4/O_2$ ratio. The values reported here of a 28 second switching time and 50:1 feed ratio, represent optimum SCMCR performance for this catalyst-adsorbent combination ($Sm_2O_3$-activated charcoal).

Substantial $CH_4$ conversion could be achieved by using a conventional recycle reactor, but matching the 65% conversion observed in the SCMCR would require a recycle reactor volume 50 to 100 times larger. In addition to the much larger catalyst inventory required, the increased contact of the recycled $C_2$ products with the $Sm_2O_3$ catalyst would result in lower $C_2$ yields through overoxidation. A significant advantage of an SCMCR over a recycle reactor is the rapid separation of the readily oxidizable $C_2$s from the oxidant and methane between each reactor-separator compartment.

Furthermore, the adsorption material in the separation zones provides an energy-efficient separation. Although the cycling of $CH_4$ around the SCMCR gives it the appearance of a recycle reactor, the SCMCR is more closely related to the countercurrent moving-bed chromatographic reactor from which it is derived. When viewed simply as a device into which reactants are introduced and from which products are extracted, the performance for the oxidative coupling reaction of methane to produce ethane and ethylene greatly exceeds that previously reported.

The invention has been described with reference to various specific and preferred embodiments and techniques. It should be understood, however, that many variations and modifications may be made while remaining within the spirit and scope of the invention.

What is claimed is:

1. A method for reacting a feed gas to produce a product and separating the product from unreacted feed gas, comprising the steps of:

(a) supplying a pressurized feed gas that includes methane and oxygen;

(b) reacting the feed gas to produce a reaction mixture which includes unreacted feed gas and a product that includes methanol and separating the product from the unreacted feed gas so as to effect a substantially simultaneous reaction and separation, wherein said reaction and separation are conducted in a plurality of compartments connected in series to form a closed loop and are carried out in separate zones of the same compartment; and (c) controlling the introduction of feed gas, the movement of unreacted feed gas, and the recovery of product such that the compartment in which the reaction and separation occurs advances sequentially and continuously around the series of compartments in the closed loop.

2. The method of claim 1 wherein the reaction zone contains a catalyst and the separation zone contains an adsorbent.

3. The method of claim 2, wherein the adsorbent includes alumina and the catalyst includes at least one of copper and cupric oxide.

4. The method of claim 3 wherein the methane/oxygen ratio of the feed gas is maintained within the range of about 15:1 to about 100:1, and wherein the substantially simultaneous reaction and separation take place at a temperature of about 350° C. to about 500° C. and at a pressure of about 30–200 atmospheres.

5. The method of claim 2 wherein the reaction zone includes a catalyst and the separation zone includes an adsorbent.

6. The method of claim 5 wherein the catalyst includes at least one of copper and cupric oxide and the adsorbent includes alumina.

7. The method of claim 6 wherein the feed gas is supplied to the inlet port such that the methane/oxygen ratio entering the compartments is maintained within the range of about 15:1 to about 100:1, and wherein the compartments are maintained at a temperature of about 350° C. to about 500° C. and at a pressure of about 30–200 atmospheres.

8. A method for reacting a feed gas to produce a product and for separating the product from unreacted feed gas, comprising the steps of:

a) providing a plurality of compartments connected in series, wherein each compartment comprises an upstream reaction zone which includes a reaction zone inlet port connected to a feed gas line, and a downstream separation zone which includes at least one separation zone outlet port; and wherein each of the separation zone outlet ports is connected to the reaction zone inlet port of the next compartment downstream in the series and the last compartment in the series is connected to the first compartment of the series to provide a closed loop;

b) supplying a pressurized feed gas that includes methane and oxygen to the reaction zone inlet port of a first one of the compartments so that the feed gas reacts in the reaction zone to produce a mixture which includes unreacted feed gas and a product that includes methanol, and so that the mixture is passed to the separation zone wherein product is separated from unreacted feed gas so as to effect a substantially simultaneous reaction and separation, and so that the unreacted feed gas exits the separation zone outlet port;

c) transferring unreacted feed gas exiting the separation zone outlet port to the reaction zone inlet port of the next compartment in the series;

d) at a time different than the unreacted feed transfer of step (c), recovering the product from the first one of the compartments;

e) just prior to the unreacted feed transfer of step (c), switching the feed gas supply from the reaction zone inlet port of the first one of the compartments to the reaction zone inlet port of the next compartment in the series, so that the feed gas and the unreacted feed gas react in the reaction zone of the next compartment to produce the mixture which includes product and unreacted feed gas, and so that the mixture is passed to the separation zone of said next compartment wherein product is separated from unreacted feed gas so as to effect a substantially simultaneous reaction and separation, and so that the unreacted feed gas exits the separation zone outlet port;

f) repeating the cycle of steps (c) through (e) in a continuous manner so that the compartment in which the reaction and separation occurs advances sequentially around the series of compartments in the closed loop.

9. A method for reacting a feed gas to produce a product and separating the product from unreacted feed gas, the method comprising the steps of:

a) providing a plurality of compartments connected in series, wherein each compartment comprises an inlet port and an outlet port defining a flowpath therebetween and a catalyst-adsorbent mixture interposed in the flowpath; and wherein each of the outlet ports is connected to the inlet port of the next compartment downstream in the series and the last compartment in the series is connected to the first compartment of the series to provide a closed loop;

b) supplying a pressurized feed gas that includes methane and oxygen to the inlet port of a first one of the compartments so that the feed gas reacts to produce a reaction mixture which includes unreacted feed gas and product that includes methanol, and so that the product is separated from the unreacted feed gas so as to effect a substantially simultaneous reaction and separation, and so that the unreacted feed gas exits the outlet port;

c) transferring unreacted feed gas exiting the outlet port of said first compartment in the series to the inlet port of the next compartment in the series;

d) after the unreacted feed transfer of step (c), recovering the product from said first one of the compartments;

e) just prior to the unreacted feed transfer of step (c), switching the feed gas supply from the inlet port of said first one of the compartments to the inlet port of said next compartment in the series, so that the feed gas and the unreacted feed gas react in said next compartment to produce the mixture which includes the product and the unreacted feed gas, and so that the product is separated from the unreacted feed gas so as to effect a substantially simultaneous reaction and separation, and so that the unreacted feed gas exits the outlet port;

f) repeating the cycle of steps (c) through (e) in a continuous manner so that the compartment in which the reaction and separation occurs advances sequentially around the series of compartments in the closed loop.

10. The method of claim 9 wherein the catalyst-absorbent mixture includes alumina and at least one of copper and cupric oxide.

11. The method of claim 10 wherein the feed gas is supplied to the inlet port such that the methane/oxygen ratio entering the compartments is maintained within the range of about 15:1 to about 100:1, and wherein the compartments are maintained at a temperature of about 350° C. to about 500° C. and at a pressure of about 30–200 atmospheres.

* * * * *

UNITED STATES PATENT AND TRADEMARK OFFICE
CERTIFICATE OF CORRECTION

PATENT NO. : 6,265,626 B1
DATED : July 24, 2001
INVENTOR(S) : Carr et al.

It is certified that error appears in the above-identified patent and that said Letters Patent is hereby corrected as shown below:

Column 5,
Line 16, delete "$A_{21}$" and insert -- $A_2$ --, therefor.
Line 27, delete "$A_n$" and insert -- $A_1$ --, therefor.
Line 48, insert -- of -- between "post" and "the".
Line 49, delete "," and insert -- . -- after "chromatograph", therefor.

Column 9,
Line 11, insert -- of -- between "presence" and "oxygen".

Signed and Sealed this

Twenty-second Day of November, 2005

JON W. DUDAS
*Director of the United States Patent and Trademark Office*